United States Patent
Ouchi

(10) Patent No.: US 6,375,650 B1
(45) Date of Patent: Apr. 23, 2002

(54) TREATING INSTRUMENT FOR ENDOSCOPE

(75) Inventor: Teruo Ouchi, Saitama (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/557,297

(22) Filed: Apr. 25, 2000

(30) Foreign Application Priority Data

Jun. 3, 1999 (JP) .......................................... 11-156031

(51) Int. Cl.[7] .............................................. A61B 17/00
(52) U.S. Cl. ........................................... 606/1; 600/139
(58) Field of Search ................................ 606/205, 167, 606/1; 600/139, 140, 144, 143

(56) References Cited

U.S. PATENT DOCUMENTS

| | | | | |
|---|---|---|---|---|
| 4,899,787 A | * | 2/1990 | Ouchi et al. ................. | 138/131 |
| 5,217,002 A | * | 6/1993 | Katsurada et al. .......... | 600/139 |
| 5,448,988 A | * | 9/1995 | Watanabe ................... | 138/118 |
| 5,536,235 A | * | 7/1996 | Yabe et al. .................. | 138/118 |
| 5,701,918 A | * | 12/1997 | Jiraki ........................ | 128/897 |
| 5,820,546 A | | 10/1998 | Ouchi | |
| 5,885,207 A | * | 3/1999 | Iwasaka ..................... | 600/139 |
| 5,921,915 A | * | 7/1999 | Aznoian et al. ............ | 600/104 |

FOREIGN PATENT DOCUMENTS

| | | |
|---|---|---|
| JP | 62144643 | 6/1987 |
| JP | 3-37605 | 8/1991 |

* cited by examiner

*Primary Examiner*—Linda C. M. Dvorak
*Assistant Examiner*—Jocelyn Ram
(74) *Attorney, Agent, or Firm*—Greenblum & Bernstein, P.L.C.

(57) ABSTRACT

A treating instrument for an endoscope includes a flexible sheath removably inserted into an instrument-inserting channel of the endoscope. A treating member is provided at the distal end of the flexible sheath to perform a treatment for an affected part or the like. The firmness of the flexible sheath in the vicinity of the distal end thereof is varied between a forward end portion extending a distance approximately equal to an extent to which the flexible sheath is projected from the instrument-inserting channel and a rear portion adjacent to the forward end portion so that the forward end portion is firmer than the rear portion.

7 Claims, 8 Drawing Sheets

TREATING INSTRUMENT FOR ENDOSCOPE

BACKGROUND OF THE INVENTION

The present disclosure relates to subject matter contained in Japanese Patent Application No. 11-156031 (filed on Jun. 3, 1999), which is expressly incorporated herein by reference in its entirety.

1. Field of the Invention

The present invention relates to a treating instrument used through an instrument passage of an endoscope.

2. Description of the Prior Art

In general, a treating instrument for an endoscope has a flexible sheath removably inserted into an instrument-inserting channel of an endoscope and a treating member provided at the distal end of the flexible sheath to perform a treatment for an affected part or the like in the patient's body. The treating instrument is used with the distal end portion thereof projected forwardly from the exit of the instrument-inserting channel at the distal end thereof.

The instrument-inserting channel of the endoscope, in which the treating instrument is inserted, is formed from a flexible tube and inserted into the insert part of the endoscope over the entire length of the latter. The insert part has a bendable portion provided at the distal end thereof. The bendable portion is bendable with a small radius of curvature by remote control.

Accordingly, the instrument-inserting channel may be bent with a small radius of curvature at a portion thereof which is located in the bendable portion. This causes an increase in frictional resistance to the insertion or removal of the treating instrument in the bendable portion. The frictional resistance acts directly as a resistance to the operation for inserting or removing the treating instrument.

Therefore, the conventional practice is to weaken the firmness of a portion of the flexible sheath that passes through the bendable portion of the endoscope (i.e. a portion of the flexible sheath that is located in the bendable portion when the treating instrument is aimed at an affected part and a portion extending forward of this portion), thereby reducing the frictional resistance to the flexible sheath when it passes through the bendable portion.

In the case of the above-described arrangement, however, the distal end portion of the flexible sheath projected from the exit of the instrument-inserting channel of the endoscope is not sufficiently firm. Therefore, when the treating instrument is aimed at an affected part and the treating member provided at the distal end of the flexible sheath is pressed against the affected part, the distal end portion of the flexible sheath may bend undesirably. In such a case, it is impossible to press the treating member against the affected part firmly to perform the intended treatment accurately.

SUMMARY OF THE INVENTION

An object of the present invention is to provide a treating instrument for an endoscope designed so that it is free from the problem of resistance to the operation for inserting or removing the treating instrument, and when the treating member is pressed against an affected part, the distal end portion of the flexible sheath is unlikely to bend, and thus the treating instrument exhibits superior aiming capability.

Other objects and advantages of the present invention will become apparent from the following detailed description of illustrated embodiments of the invention.

According to the present invention, there is provided a treating instrument for an endoscope which includes a flexible sheath removably inserted into an instrument-inserting channel of the endoscope. A treating member is provided at the distal end of the flexible sheath to perform a treatment for an affected part or the like. The firmness of the flexible sheath in the vicinity of the distal end thereof is varied between a forward end portion extending a distance approximately equal to an extent to which the flexible sheath is projected from the instrument-inserting channel and a rear portion adjacent to the forward end portion so that the forward end portion is firmer than the rear portion.

BRIEF DESCRIPTION OF THE DRAWINGS

The present invention may be more fully understood from the description of preferred embodiments of the invention set forth below, together with the accompanying drawings, in which.

DESCRIPTION OF THE EMBODIMENTS

Embodiments of the present invention will be described below with reference to the accompanying drawings.

Figure 1:
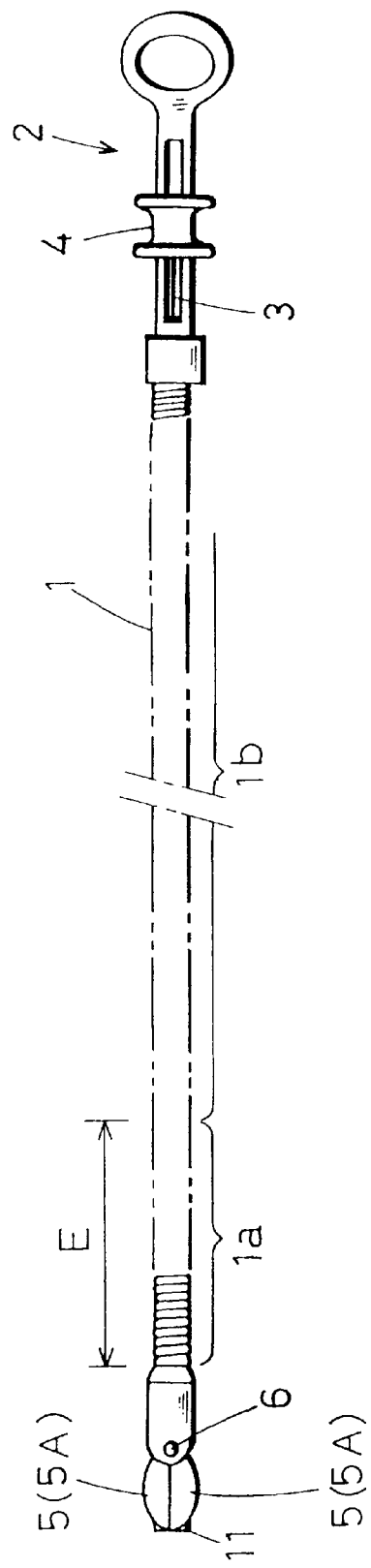
FIG. 1 is a side view of a biopsy forceps for an endoscope according to a first embodiment of the present invention.
Figure 2:
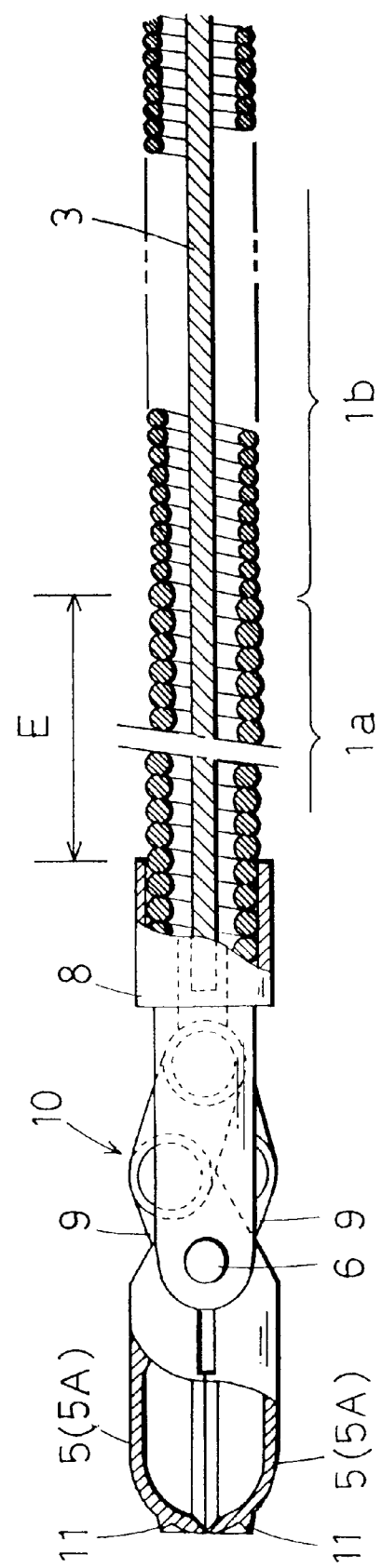
FIG. 2 is a sectional side view showing the distal end portion of the biopsy forceps according to the first embodiment of the present invention.

FIGS. 1 and 2 show a biopsy forceps for an endoscope, which is one of treating instruments used with an endoscope. FIG. 1 shows the whole arrangement of the biopsy forceps. FIG. 2 is an enlarged view of the distal end portion of the biopsy forceps.

A flexible sheath 1 is removably inserted into an instrument-inserting channel of an endoscope. The flexible sheath 1 is formed from a coil pipe that is formed by close-winding a thin stainless steel wire, for example, into a helical shape with a uniform diameter.

The flexible sheath 1 has a firm portion 1a (with a length E) at the distal end thereof and a non-firm portion 1b adjacent to the rear end of the firm portion 1a. The firm portion 1a is firm in comparison to the non-firm portion 1b. More specifically, the firm portion 1a is formed by using a thin stainless steel wire having a relatively large wire diameter. The non-firm portion 1b is formed by using a thin stainless steel wire having a relatively small wire diameter.

Figure 3:
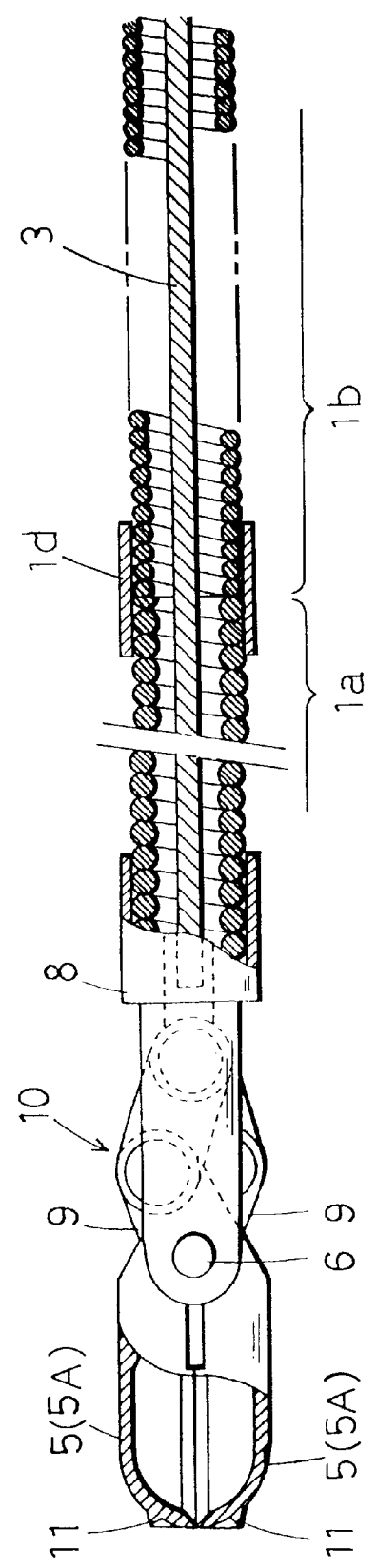
FIG. 3 is a sectional side view showing a modification of the distal end portion of the biopsy forceps according to the first embodiment of the present invention.

In this embodiment, the wire that forms the firm portion 1a and the wire that forms the non-firm portion 1b are contiguous with each other. However, as shown in FIG. 3, the wire forming the firm portion 1a and the wire forming the non-firm portion 1b may be produced as two separate members and connected in series by a connecting pipe 1d or the like.

As shown in FIG. 1, an instrument operating part 2 is connected to the proximal end of the flexible sheath 1. A slider 4 is slidably provided on the instrument operating part 2 to advance or retract a control wire 3 axially movably inserted in the flexible sheath 1 over the entire length of the latter.

A pair of tissue-taking cups 5A, which are a pair of treating members 5, are attached to the distal end of the flexible sheath 1. The tissue-taking cups 5A are rotatable about a shaft 6 so as to be opened or closed about the shaft 6. When the control wire 3 is advanced or retracted by sliding the slider 4 at the instrument operating part 2, the tissue-taking cups 5A are opened or closed about the shaft 6 in a fan-like manner.

As shown in FIG. 2, the pair of tissue-taking cups 5A are each formed in a hemispherical shape somewhat elongated in the axial direction. When the pair of tissue-taking cups 5A are closed together, the distal end surfaces thereof form one spherical surface. The tissue-taking cups 5A have cutting edges formed on the ridges of their mutually opposing opening portions. A forwardly facing pointed projection 11 is provided on the surface of the distal end portion of each tissue-taking cup 5A.

The shaft 6 is mounted on a distal end portion of a distal end block 8 firmly connected to the distal end of the flexible sheath 1. The rear half of the distal end block 8 (the right-hand portion as viewed in FIG. 2) is formed in the shape of a cylinder. The front half of the distal end block 8 is slit in the center to form a pair of parallel arms.

Each tissue-taking cup 5A has an integrally formed arm 9 extending rearward from a position where the tissue-taking cup 5A is engaged with the shaft 6. The arms 9 of the tissue-taking cups 5A are connected to a pantograph-shaped link mechanism 10 placed in the slit of the distal end block 8.

The distal end of the control wire 3 is firmly connected to the rear end portion of the link mechanism 10. When the control wire 3 is pushed from the instrument operating part 2, the link mechanism 10 is activated to open the tissue-taking cups 5A about the shaft 6 in a fan-like manner.

If the control wire 3 is pulled from the instrument operating part 2 in this state, the tissue-taking cups 5A are closed, thereby allowing a piece of tissue for a biopsy specimen or the like to be taken into the tissue-taking cups 5A.

Figure 4:
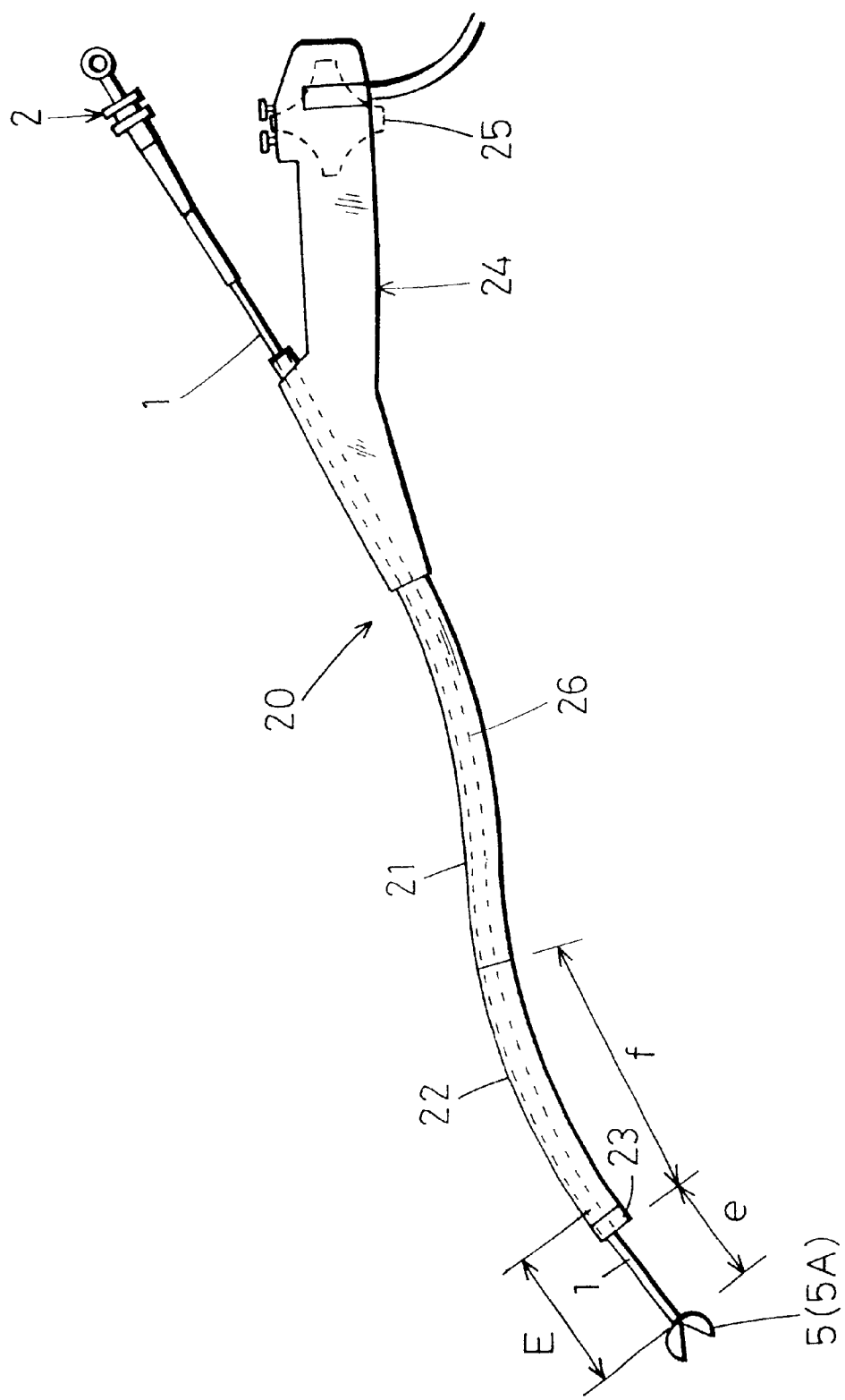
FIG. 4 is a side view showing the biopsy forceps according to the first embodiment of the present invention in a state where the biopsy forceps is inserted into an instrument-inserting channel of an endoscope.

FIG. 4 shows the biopsy forceps according to the above-described embodiment in a state where it is set in an endoscope 20. The endoscope 20 includes a flexible insert part 21 having a bendable portion 22 formed at the distal end thereof. A distal end block 23 is secured to the distal end of the bendable portion 22. The distal end block 23 is provided with a viewing window, etc.

An endoscope control part 24 is provided with a control knob 25 for bending the bendable portion 22 at a desired angle in a desired direction by remote control. An instrument-inserting channel 26, into which the flexible sheath 1 is removably inserted, is formed from a flexible tube and inserted in the flexible insert part 21 to extend over the entire length of the insert part 21 from the inside of the bendable portion 22. The entrance of the instrument-inserting channel 26 is positioned in the endoscope control part 24. The exit of the instrument-inserting channel 26 is positioned in the distal end block 23.

The length f of the bendable portion 22 is of the order of from 3 to 5 centimeters in the case of an endoscope for bronchoscopy. In the case of an endoscope for inspection of the digestive tract, the length f of the bendable portion 22 is of the order of from 5 to 12 centimeters. The length e by which the flexible sheath 1 of the biopsy forceps projects from the exit of the instrument-inserting channel 26 is of the order of from 2 to 8 centimeters.

The length E of the firm portion 1a of the flexible sheath 1 is set substantially equal to the projecting length e of the flexible sheath 1 from the instrument-inserting channel 26 (preferably, the length E is slightly longer than the length e).

Figure 5:
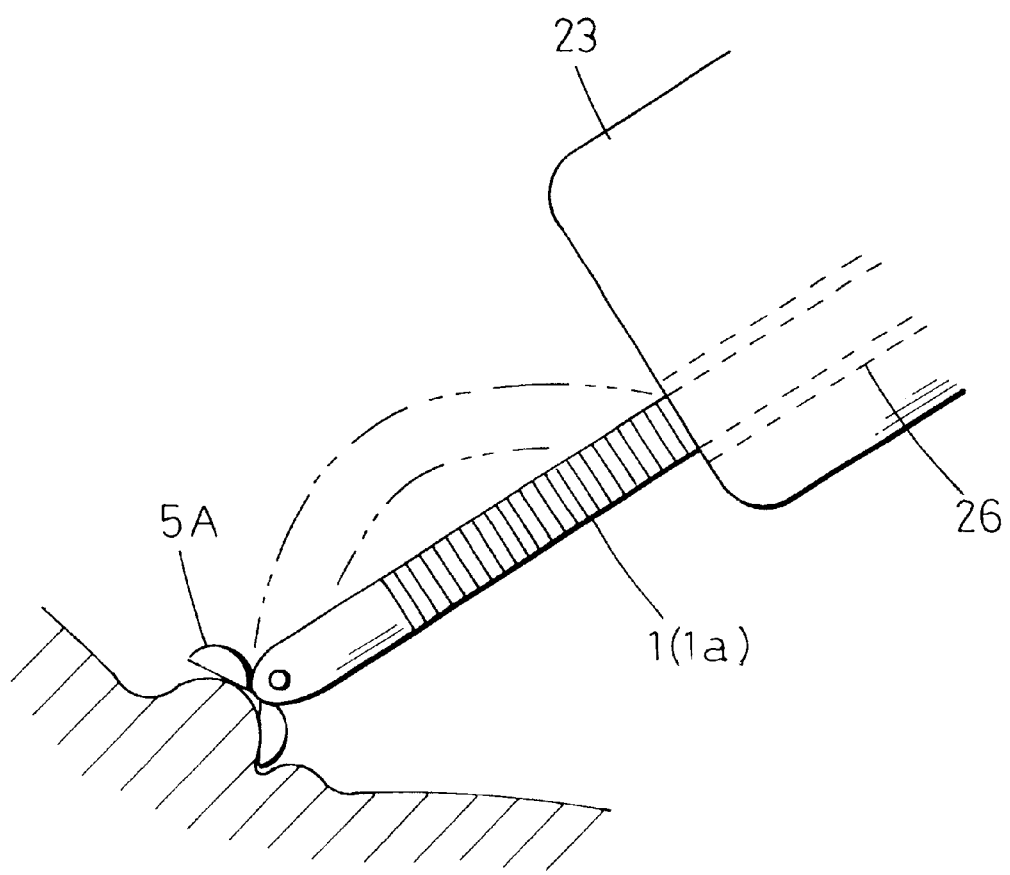
FIG. 5 is a schematic view showing the distal end portion of the biopsy forceps according to the first embodiment of the present invention in a state where the biopsy forceps is actually used.

FIG. 5 schematically shows the way in which a piece of tissue is taken for a biopsy specimen with the above-described biopsy forceps through the instrument-inserting channel 26 of the endoscope. The portion of the flexible sheath 1 of the biopsy forceps that projects from the distal end of the instrument-inserting channel 26 is the firm portion 1a. Therefore, when the tissue-taking cups 5A are strongly pressed against an affected part, the firm portion 1a will not bend as shown by the chain double-dashed lines. Accordingly, a bioptic operation can be performed smoothly with the tissue-taking cups 5A pressed against the affected part accurately.

Because the portion of the flexible sheath 1 of the biopsy forceps that is located in the bendable portion 22 is the non-firm portion 1b, there is a minimal resistance to the operation of advancing or retracting the flexible sheath 1 to aim the tissue-taking cups 5A at the affected part. Accordingly, a delicate advancing-retracting operation can be surely performed.

Figure 6:
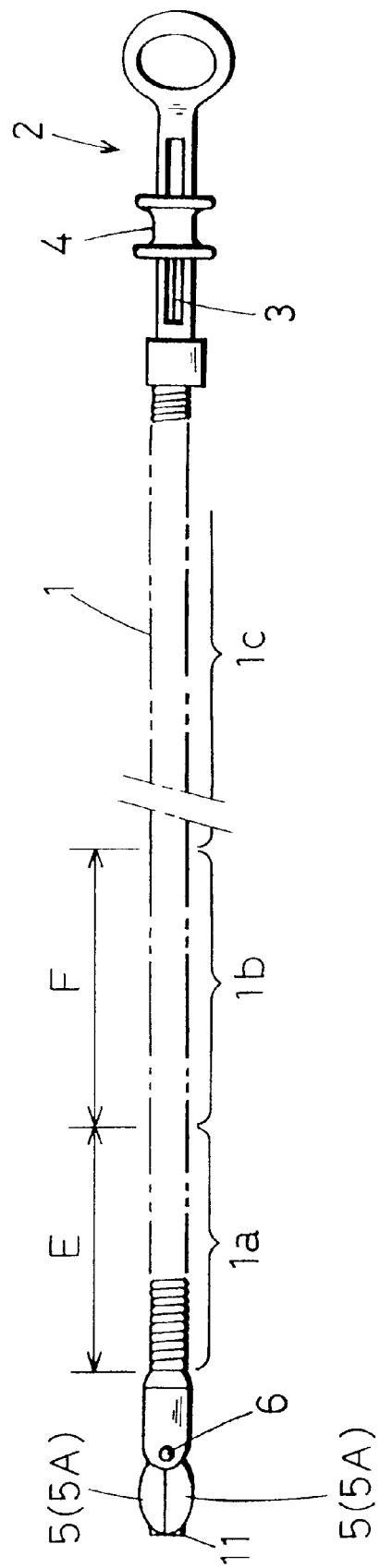
FIG. 6 is a side view of a biopsy forceps according to a second embodiment of the present invention.

FIG. 6 shows a second embodiment in which the present invention is applied to a biopsy forceps. In this embodiment, a rear firm portion 1c is formed at the rear of the non-firm portion 1b of the flexible sheath 1. The rear firm portion 1c is firmer than the non-firm portion 1b.

With the above-described arrangement, when the flexible sheath 1 is pushed into the instrument-inserting channel 26, the flexible sheath 1 is unlikely to buckle. The firmness of the rear firm portion 1c and that of the firm portion 1a, which is at the distal end of the flexible sheath 1, may be equal to or different from each other.

The length F of the non-firm portion 1b of the flexible sheath 1 should be set so that when the biopsy forceps is used as shown in FIG. 5, the non-firm portion 1b is located in the bendable portion 22. For example, the length F of the non-firm portion 1b is 10 to 15 centimeters.

Figure 7:
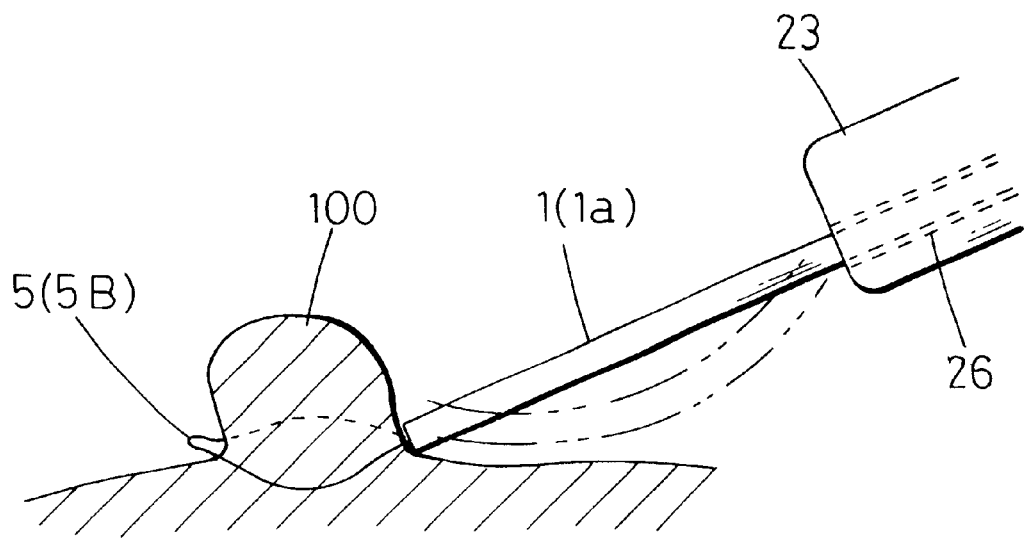
FIG. 7 is a side view showing the distal end portion of a high-frequency snare for an endoscope according to a third embodiment of the present invention in a state where the high-frequency snare is actually used.

FIG. 7 shows a high-frequency snare for an endoscope, to which the present invention is applied, in a state where a polyp 100 is bound tight with the high-frequency snare passed through the instrument-inserting channel 26 of the endoscope. In this case, a flexible sheath 1 is formed from an electrically insulating tube, for example, a tetrafluoroethylene resin tube. A treating member 5 is a snare loop 5B formed from an electrically conductive metal wire.

The high-frequency snare is the same as the above-described biopsy forceps in that the flexible sheath 1 is provided with a firm portion 1a and a non-firm portion 1b and also in terms of the lengths of the firm portion 1a and the non-firm portion 1b.

Consequently, when the flexible sheath 1 is pressed against the mucous membrane surface strongly to encircle the polyp 100 with the snare loop 5B, the flexible sheath 1 will not bend as shown by the chain double-dashed lines. Therefore, the polyp 100 can be surely and readily bound tight with the snare loop 5B.

Figure 8:
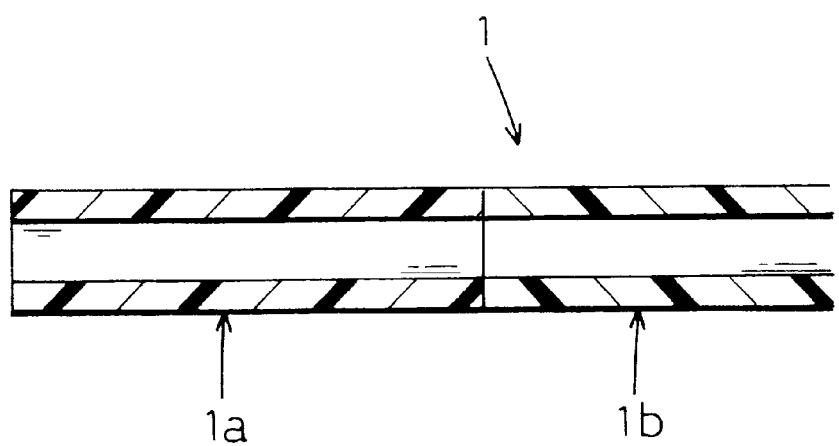
FIG. 8 is a sectional side view showing a first structural example of a sheath used in the high-frequency snare according to the third embodiment of the present invention.
Figure 9:
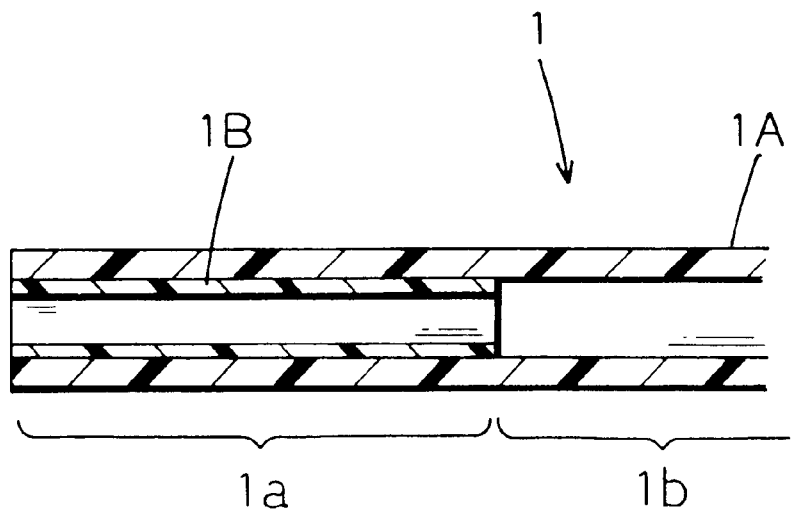
FIG. 9 is a sectional side view showing a second structural example of a sheath used in the high-frequency snare according to the third embodiment of the present invention.
Figure 10:
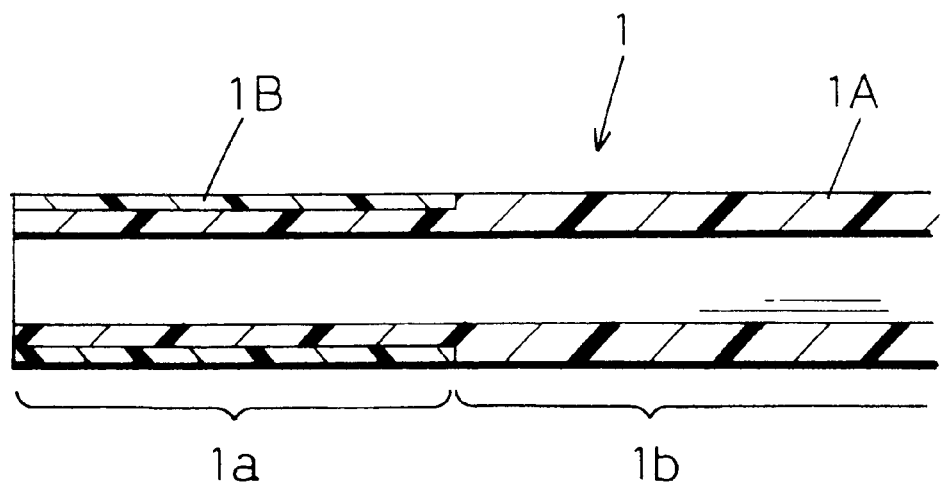
FIG. 10 is a sectional side view showing a third structural example of a sheath used in the high-frequency snare according to the third embodiment of the present invention.

It should be noted that the flexible sheath 1 of the high-frequency snare, which is provided with the firm portion 1a and the non-firm portion 1b, may be formed by series-connecting tubes that are different in hardness from each other, as shown in FIG. 8. Alternatively, as shown in FIGS. 9 and 10, a first tube 1A and a second tube 1B, which are different in hardness from each other, may be partially superimposed on one another to form the flexible sheath 1. That is, the second tube 1B is fitted to the inner or outer periphery of a part of the first tube 1A. In this case, the total wall thickness of the superimposed portion may be the same as the wall thickness of the other portion of the flexible sheath 1. It is also possible to form the flexible sheath 1 by covering the outer surface of the coil pipe used in the above-described biopsy forceps with an insulating tube.

It should be noted that the present invention is not necessarily limited to the foregoing embodiments but can also be applied to various treating instruments other than biopsy forceps and snares.

In the treating instrument for an endoscope according to the present invention, the firmness of the flexible sheath is varied between a forward end portion extending a distance approximately equal to an extent to which the flexible sheath is projected from the instrument-inserting channel and a rear portion adjacent to the forward end portion so that the forward end portion is firmer than the rear portion. Consequently, when the treating member provided at the distal end of the flexible sheath is pressed against an affected part, the distal end of the flexible sheath is unlikely to bend. Accordingly, the treating instrument can be readily aimed at the affected part. Thus, the treating instrument exhibits superior aiming capability. Moreover, there is a minimal resistance to the passage of the flexible sheath through the bendable portion of the endoscope when the treating instrument is aimed at the affected part. Therefore, the treating instrument is free from the problem of resistance to the operation for inserting or removing the treating instrument and therefore easy to use.

While the invention has been described by reference to specific embodiments chosen for purposes of illustration, it should be apparent that numerous modifications could be made thereto by those skilled in the art without departing from the basic concept and scope of the invention.

What is claimed is:

1. A treating instrument for an endoscope comprising a flexible sheath adapted to be removably inserted into an instrument-inserting channel of the endoscope, and a treating member provided at a distal end of said flexible sheath to perform a treatment for an affected part of a body, wherein the firmness of the distal end of said flexible sheath is varied between a forward portion and a rear portion, said forward portion being approximately equal in length to the greatest distance that the sheath can be projected from said instrument-inserting channel, and said rear portion being adjacent to said forward portion, wherein said forward portion is firmer than said rear portion.

2. A treating instrument for an endoscope according to claim 1, wherein said flexible sheath is a coil pipe comprising a metal wire wound into a helical shape with a uniform diameter, said coil pipe varying in wire diameter at an intermediate portion thereof so that the firmness of said flexible sheath changes at the intermediate portion.

3. A treating instrument for an endoscope according to claim 1, wherein said flexible sheath comprises a plurality of coil pipes, each of said coil pipes comprising a metal wire wound in a helical shape with a uniform diameter, adjacent ones of said coil pipes comprising wires of different diameters and being connected in series so that the firmness of said flexible sheath changes at an intermediate portion thereof.

4. A treating instrument for an endoscope according to claim 1, wherein said flexible sheath comprises a plurality of flexible tubes different in hardness from each other, said flexible tubes being connected in series so that the firmness of said flexible sheath changes at an intermediate portion thereof.

5. A treating instrument for an endoscope according to claim 1, wherein said flexible sheath comprises a first flexible tube and a second flexible tube, said second flexible tube being fitted to an inner or outer periphery of a part of said first flexible tube so that the firmness of said flexible sheath changes at,an intermediate portion thereof.

6. A treating instrument for an endoscope according to claim 1, wherein the length of said forward end portion of said flexible sheath is between 2 centimeters and 8 centimeters.

7. A treating instrument for an endoscope according to claim 1, wherein the firmness of said flexible sheath also changes within said rear portion, wherein a proximal portion of said rear portion is firmer than a distal portion of said rear portion.

* * * * *